United States Patent [19]

Patil et al.

[11] Patent Number: 5,221,765
[45] Date of Patent: Jun. 22, 1993

[54] RACEMIZATION PROCESS FOR AN OPTICALLY ACTIVE CARBOXYLIC ACID OR ESTER THEREOF

[75] Inventors: Deepak R. Patil; Azfar A. Choudhury; Abbas Kadkhodayan, all of Orangeburg, S.C.

[73] Assignee: Ethyl Corporation, Richmond, Va.

[21] Appl. No.: 825,150

[22] Filed: Jan. 24, 1992

[51] Int. Cl.$^5$ .............................. C07B 55/00
[52] U.S. Cl. ........................ 562/401; 548/572; 549/499; 549/79; 560/10; 560/15; 560/51; 560/56; 560/61; 560/100; 560/105; 560/122; 560/123; 560/124; 560/125; 560/126; 560/152; 560/226; 560/227; 560/265
[58] Field of Search ............ 562/401; 549/599; 560/10, 15, 51, 56, 61, 100, 105, 122, 123, 124, 125, 126, 152, 226, 227, 265; 548/572

[56] References Cited

U.S. PATENT DOCUMENTS

| | | |
|---|---|---|
| 4,767,880 | 8/1988 | Wullbrandt et al. ............ 560/61 |
| 4,769,486 | 9/1988 | Harada et al. ................. 562/401 |
| 4,946,997 | 8/1990 | Larsen et al. ................. 562/401 |

Primary Examiner—José G. Dees
Assistant Examiner—Vera C. Clarke
Attorney, Agent, or Firm—Richard J. Hammond

[57] ABSTRACT

A method for racemizing an optically active carboxylic acid, or ester thereof, of the formula:

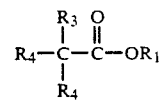

where $R_1$ is hydrogen or $C_1$ to $C_6$ linear or branched alkyl; $R_2$, $R_3$ and $R_4$ are different and are hydrogen or $C_1$ to $C_6$ linear or branched alkyl, $C_1$ to $C_6$ linear or branched haloalkyl, aralkyl, cycloalkyl, alkyl substituted cycloalkyl, $C_6$ to $C_{10}$ aryl, $C_1$ to $C_6$ linear or branched alkoxy, $C_6$ to $C_{10}$ aryloxy, $C_1$ to $C_6$ alkylthio, $C_2$ to $C_8$ cycloalkylthio, $C_6$ to $C_{10}$ arylthio, $C_6$ to $C_{10}$ arylcarbonyl, $C_4$ to $C_8$ cycloalkenyl, trifluoromethyl, halo, $C_4$ to $C_5$ heteroaryl, $C_{10}$ to $C_{14}$ aryl, or biphenyl unsubstituted or substituted with methyl or halo, comprising heating said optically active carboxylic acid or ester thereof in the presence of water at a temperature of from about 75° C. to about 200° C. in the presence of a catalytically effective amount of an aliphatic, aromatic or mixed aliphatic and aromatic tertiary amine for a time sufficient to racemize said carboxylic acid or ester thereof.

18 Claims, No Drawings

RACEMIZATION PROCESS FOR AN OPTICALLY ACTIVE CARBOXYLIC ACID OR ESTER THEREOF

FIELD OF THE INVENTION

This invention relates to a process for converting an enantiomeric form of certain aliphatic carboxylic acids into a racemic mixture of enantiomers. This invention specifically relates to the racemization of one of the enantiomers of profen-type carboxylic acids or ester.

BACKGROUND OF THE INVENTION

Profen-types of compounds are typically defined as substituent, usually α- to the carboxylic function.

These carboxylic acids have an asymmetric carbon atom (the carbon atom adjacent to the carbonyl group) that typically produces a racemic mixture of these acids [a mixture of both the (+) and (−) or dextro and levo rotatory forms]. For example, ibuprofen [(2-(4-isobutyl-phenyl)propionic acid)], a commercially and pharmaceutically important chemical compound, is typically produced and sold as the racemic mixture. Many other of the pharmaceutically-active profen drugs are also produced as racemates and administered in this form. However, it is well known that the physiological utility of the racemic mixtures is almost exclusively focused on one enantiomer, the other having either no effect or even diminishing the effect of the active enantiomer. Thus the S(+) form of ibuprofen is physiologically active in reducing inflammation and in providing an analgesic effect. See, for example, U.S. Pat. Nos. 4,851,444 and 4,877,620. The R(−) enantiomer is devoid of activity for these indications, although it is, in part, converted in vivo into the S(+) compound. Other profens, i.e., naproxen, are only prescribed as the single enantiomer.

OBJECTS OF THE INVENTION

Disposal of the undesired enantiomer is not environmentally or economically desirable. Accordingly, it is an object of this invention to provide a process whereby the inactive or undesirable enantiomer of these carboxylic acids may be converted into the other usable, desirable enantiomer.

It is a further object of this invention to carry out the conversion of one enantiomer of these carboxylic acids into the other enantiomer in an efficient and economical manner.

These and other objects of the present invention are more completely described hereafter in the description of the preferred embodiment.

DESCRIPTION OF THE PREFERRED EMBODIMENTS

The carboxylic acids and esters useful in the process of the present invention have the formula:

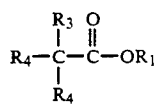
  I where $R_1$ is hydrogen or $C_1$ to $C_6$ linear or branched alkyl, $R_2$, $R_3$ and $R_4$ are different and are hydrogen or $C_1$ to $C_6$ linear or branched alkyl, e.g., methyl or ethyl; $C_1$ to $C_6$ linear or branched haloalkyl, e.g., chloromethyl, fluoromethyl, chloroethyl, fluoroethyl; aralkyl, e.g., benzyl; cycloalkyl, e.g., cyclopropyl, cyclobutyl, cyclopentyl, or cyclohexyl; alkyl substituted cycloalkyl, e.g., methylcyclohexyl; $C_6$ to $C_{10}$ aryl, e.g., phenyl unsubstituted or substituted with, for example, methyl, dimethyl, or butyl, especially isobutyl or phenyl substituted with $C_1$ to $C_4$ alkylthio, $C_1$ to $C_4$ alkoxy, cyano or halo, e.g., fluoro or chloro; $C_1$ to $C_6$ linear or branched alkoxy, e.g., methoxy, ethoxy, propoxy, or butoxy; $C_6$ to $C_{10}$ aryloxy, e.g., phenoxy or phenoxy substituted with, for example, methyl, dimethyl, butyl or isobutyl or phenoxy substituted with $C_1$ to $C_4$ alkylthio, $C_1$ to $C_4$ alkoxy, cyano or halo; $C_1$ to $C_6$ alkylthio, e.g., methylthio; $C_2$ to $C_8$ cycloalkylthio; $C_6$ to $C_{10}$ arylthio; $C_6$ to $C_{10}$ arylcarbonyl, e.g., benzoyl; $C_4$ to $C_8$ cycloalkenyl, e.g., cyclohexenyl; trifluoromethyl; halo, e.g., fluoro or chloro; $C_4$ to $C_8$ heteroaryl, e.g., furyl, pyrrolyl, or thienyl; or $C_{10}$ to $C_{14}$ aryl, e.g., naphthyl or naphthyl substituted with $C_1$ to $C_4$ alkyl, e.g., methyl, $C_1$ to $C_4$ alkoxy, e.g., ethoxy or halo; or biphenyl unsubstituted or substituted with methyl or halo, especially fluoro.

Preferred compounds of formula I are those of the formula:

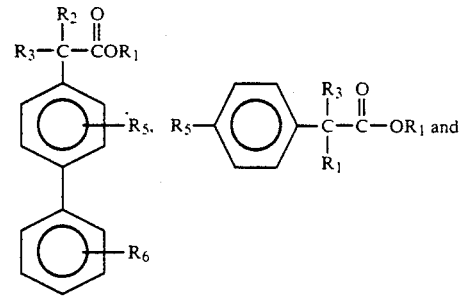

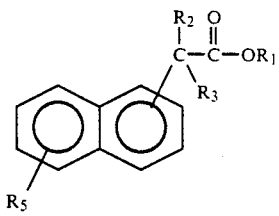

where $R_1$, $R_2$ and $R_3$ are as previously defined and $R_5$ and $R_6$ are $C_1$ to $C_4$ linear or branched alkyl, $C_1$ to $C_4$ linear or branched alkoxy or halo.

The process of the present invention is particularly applicable to 2 (4-isobutylphenyl)propionic acid and especially in racemization of the R(−) isomer.

The process involves using one of the enantiomeric forms (or an enantiomerically enriched mixture) of such carboxylic acids as a starting material and subjecting this starting material to the process of the present invention whereby conversion of one enantiomer to the other is effected. It should functions to achieve a racemic mixture of the enantiomers, i.e., it is a racemization process.

The process involves racemizing the enantiomer in the presence of water at a temperature of from about 75° C. to about 200° C. Preferably, the process is carried out at about 110° C. to about 150° C., most preferably about 110° C. to about 140° C. The time of conversion to the racemic mixture is dramatically affected by adding to the aqueous solution a catalytically effective amount of a tertiary amine that is aliphatic, aromatic or mixed aliphatic and aromatic. Aliphatic tertiary amines are those having three identical or different $C_1$ to $C_6$ linear or branched alkyl groups attached to the nitrogen atom and include, for example, trimethylamine, triethylamine, tri-n-propylamine, methyldiethylamine, dimethylethylamine, tri-n-butylamine and the like.

Aromatic amines are those where phenyl, substituted phenyl, naphthyl or substituted naphthyl groups, either the same or different, are bound to the nitrogen atom. These include triphenylamine, trinaphthylamine, ortho, meta or para-substituted tolyldiphenylamine, phenyl, di(ortho, meta, or para-substituted) tolylphenylamine and the like.

Mixed aliphatic/aromatic amines are also useful in this process such as, for example, dimethylphenylamlne.

The amounts of such catalytic amine added to the solution can vary from about 00.01% to about 10.0% of such amine based on the mole % of carboxylic acid enantiomer to be converted. Preferably, the amount of amine is from about 0.05 mole % to about 0.5 % mole based moles of carboxylic acid, most preferably 0.075 mole % to about 0.25 mole %.

By using the above disclosed catalytic amines, the time period to achieve a racemic mixture is reduced to from about 4 to about 24 hours, depending on the amount of excess enantiomer in the starting material. For example, with a starting material of 100% enantiomer periods of conversion to the racemic mixture are about 20 to 24 hours. Enantiomerically enriched starting materials reach the racemization maximum more quickly, e.g., a composition comprising 70% R($-$) enantiomer and 30% S($+$) enantiomer will achieve the 50:50 racemization in about 10 to about 12 hours.

In addition to the tertiary amine catalyst useful to enhance the rate of racemization, it has been discovered that the presence of an aromatic or aliphatic hydrocarbon in amounts noted earlier for the amine catalyst further catalyze the process. Thus, by using hexane, heptane, benzene, toluene or xylene as a co-catalyst, the rates of racemization can be decreased by 10 to 20% from those rates shown about using solely the amine catalyst.

In addition to the tertiary amine catalyst and the said hydrocarbon, it has been discovered that the presence of water eliminates the by-product formation, thus increased yield As indicated above, the process of the present invention is useful for conversion of one of the enantiomeric forms of the disclosed aliphatic carboxylic acid into the other only up to the point of achieving a racemic mixture of enantiomers. The racemic mixture is, of course, useful as is or it may be subject to other processes to separate the enantiomeric mixture.

EXAMPLES

The following examples are illustrative of the process of the present invention.

Generation of Mother Liquor

To a 12-liter flask equipped with an agitator, thermometer reflux condenser and an addition funnel, were charged 824 grams of racemic ibuprofen and 8 liters of hexane. The slurry was agitated and heated to dissolve the ibuprofen to which was added 242 grams of S-methylbenzyl amine over 4 hours. After agitating for two more hours, the resultant slurry was filtered and washed with hexane to isolate the solids. The filtrates were combined and heated to remove most of the hexane. The syrupy liquid was evaporated to dryness and the R-enantiomer enriched ibuprofen was recovered (411 grams). The analysis shows these solids contain 98.9% ibuprofen (78% R-enantiomer and 1.1% S-methylbenzyl amine).

EXAMPLE 1

50 grams of R-enantiomer enriched solids (78% R-enantiomer) containing 49.5 grams ibuprofen and 0.5 grams S-methylbenzyl amine, 12 grams triethylamine were charged to a reactor and heated to 120° C. under pressure for 4 hours. Upon cooling, the solids from the reactor were removed and analyzed. The analysis is as follows:

| | |
|---|---|
| Total solids recovered = | 49.5 grams |
| Ibuprofen = | 78.3% |
| Ibuprofen - S-methylbenzyl amide = | 2.3% |
| S-methylbenzyl amine = | 0.0% |
| Triethylamine = | 19.4% |
| % S-enantiomer = | 49.4% |

The yield of racemized ibuprofen is 97.1% as the remaining ibuprofen is considered as process losses to amide formation.

EXAMPLE 2

The procedure of Example 1 was repeated except for that 12 grams of triethylamine were replaced by 100 grams of hexane. The mixture was treated at 120° C. under pressure for 4 hours. Upon cooling, the entire contents of the reactor were dissolved in 1,000 mL of hexane and analyzed. The analysis of this solution on a solvent-free basis is as follows:

| | |
|---|---|
| Ibuprofen = | 97.5% |
| S-methylbenzyl amine = | 0.0% |
| Ibuprofen - S-methylbenzyl amide = | 2.5% |
| % S-enantiomer = | 34.0% |

The material was essentially unaffected by the racemization procedure.

EXAMPLE 3

The procedure of Example 1 was repeated. However, in addition to the solids and triethylamine, 1000 mL of hexane were charged to the reactor. The mixture was heated to 120° C. and held under pressure for 4 hours. Upon cooling the reactor, the contents of the reactor were analyzed and are as follows on a solvent-free basis:

| | |
|---|---|
| Ibuprofen = | 78.2% |
| S-methylbenzyl amine = | 0.0% |
| Ibuprofen - S-methylbenzyl amide = | 2.3% |
| Triethylamine = | 19.5% |
| % S-enantiomer = | 49.2% |

The yield of racemized ibuprofen is 97% and the remaining ibuprofen was lost to amide formation.

EXAMPLE 4

50 grams of solids from the same batch used in Examples 1 through 3 were charged to the reactor and treated at 20° C. for 4 hours. Upon cooling, the solids were analyzed. The analysis was very similar to the analysis from Example 2. No racemization had occurred.

EXAMPLE 5

50 grams of solids from the same batch used in Example 1 through 4, 12 grams triethylamine and 10 grams of water were charged to a reactor. The reactor contents were treated at 120° C. for 4 hours. The analysis showed that partial racemization had taken place and no amide had formed. The S-enantiomer content of the ibuprofen was 44%.

EXAMPLE 6

In addition to the charges from Example 5, 50 mL of hexane were charged to the reactor and treated at 120° C. for 4 hours under pressure. The analysis showed that the ibuprofen had racemized and no amide was formed. Ex. solvent analysis follows:

| Total solids recovered = | 49.4 grams |
|---|---|
| Ibuprofen = | 78.5% |
| S-methylbenzyl amine = | 1.4% |
| Triethylamine = | 19.9% |
| S-enantiomer = | 49.4% |

The yields of racemized ibuprofen and S-methylbenzyl amine are essentially quantitative.

We claim:

1. A method for racemizing an optically active carboxylic acid, or ester thereof, of the formula:

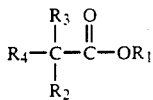

where $R_1$ is hydrogen or $C_1$ to $C_6$ linear or branched alkyl; $R_2$, $R_3$ and $R_4$ are different and are hydrogen or $C_1$ to $C_6$ linear or branched alkyl, $C_1$ to $C_6$ linear or branched haloalkyl, aralkyl, cycloalkyl, alkyl substituted cycloalkyl, $C_1$ to $C_6$ linear or branched alkoxy, $C_6$ to $C_{10}$ aryloxy, $C_1$ to $C_6$ alkylthio, $C_2$ to $C_8$ cycloalkylthio, $C_6$ to $C_{10}$ arylthio, $C_6$ to $C_{10}$ arylcarbonyl, $C_4$ to $C_8$ cycloalkenyl, trifluoromethyl, halo, $C_4$ to $C_5$ heteroaryl, or $C_6$ to $C_{14}$ aryl, comprising heating an aqueous solution of said optically active carboxylic acid or ester thereof at a temperature of from about 75° C. to about 200° C. in the presence of a catalytically effective amount of an aliphatic, aromatic or mixed aliphatic and aromatic tertiary amine for a time sufficient to racemize said carboxylic acid or ester thereof.

2. The method according to claim 1 wherein said temperature is from about 100° C. to about 150° C.

3. The method according to claim 1 wherein said temperature is from about 110° C. to about 140° C.

4. The method according to claim 1 wherein said tertiary amine is aliphatic.

5. The method according to claim 4 wherein said tertiary amine is selected from the group consisting of trimethylamine, triethylamine, tri-n-propylamine, methyldiethylamine, dimethylethylamine and tri-n-butylamine.

6. The method according to claim 1 wherein said tertiary amine is N,N-dimethylaniline.

7. The method according to claim 1 wherein an aliphatic hydrocarbon is added as a cocatalyst.

8. The method according to claim 7 wherein said aliphatic hydrocarbon is a $C_5$ to $C_8$ aliphatic hydrocarbon.

9. The method according to claim 8 wherein said aliphatic hydrocarbon is hexane.

10. A method for racemizing R(−)-ibuprofen comprising heating an aqueous solution of said ibuprofen at a temperature of from about 75° C. to about 200° C. in the presence of a catalytically effective amount of an aliphatic, aromatic or mixed aliphatic and aromatic tertiary amine for a time sufficient to racemize said ibuprofen.

11. The method according to claim 10 wherein said temperature is from about 100° C. to about 150° C.

12. The method according to claim 10 wherein said temperature is from about 110° C. to about 140° C.

13. The method according to claim 10 wherein said tertiary amine is aliphatic.

14. The method according to claim 13 wherein said tertiary amine is selected from the group consisting of trimethylamine, triethylamine, tri-n-propylamine, methyldiethylamine, dimethylethylamine and tri-n-butylamine.

15. The method according to claim 10 wherein said tertiary amine is N,N-dimethylaniline.

16. The method according to claim 10 wherein an aliphatic hydrocarbon is added as a cocatalyst.

17. The method according to claim 16 wherein said cocatalyst is a $C_5$ to $C_8$ aliphatic hydrocarbon.

18. The method according claim 17 wherein said cocatalyst is hexane.

* * * * *